(12) United States Patent
Khizar

(10) Patent No.: US 11,725,336 B2
(45) Date of Patent: Aug. 15, 2023

(54) SANITATION DEVICE

(71) Applicant: WHIRLPOOL CORPORATION, Benton Harbor, MI (US)

(72) Inventor: Muhammad Khizar, St. Joseph, MI (US)

(73) Assignee: Whirlpool Corporation, Benton Harbor, MI (US)

( * ) Notice: Subject to any disclaimer, the term of this patent is extended or adjusted under 35 U.S.C. 154(b) by 0 days.

(21) Appl. No.: 17/382,682

(22) Filed: Jul. 22, 2021

(65) Prior Publication Data

US 2021/0355627 A1 Nov. 18, 2021

Related U.S. Application Data

(62) Division of application No. 16/144,453, filed on Sep. 27, 2018, now Pat. No. 11,085,147.

(51) Int. Cl.
| *A61L 2/10* | (2006.01) |
|---|---|
| *D06F 34/26* | (2020.01) |
| *D06F 58/38* | (2020.01) |
| *D06M 10/00* | (2006.01) |
| *D06F 39/12* | (2006.01) |
| *D06F 58/20* | (2006.01) |

(52) U.S. Cl.
CPC ............. *D06M 10/001* (2013.01); *A61L 2/10* (2013.01); *D06F 39/12* (2013.01); *D06F 58/203* (2013.01)

(58) Field of Classification Search
CPC .. D06F 34/26; D06F 2103/34; D06F 2105/12; D06F 2105/22; D06F 58/38; D06F 2101/16; A47L 15/4445; D06M 10/001
See application file for complete search history.

(56) References Cited

U.S. PATENT DOCUMENTS

| 4,182,050 A | 1/1980 | Righi |
|---|---|---|
| 5,664,340 A | 9/1997 | Brown |
| 6,958,693 B2 | 10/2005 | Rothgeb et al. |
| 8,276,290 B2 | 10/2012 | Uhara et al. |
| 9,732,462 B2 | 8/2017 | Kim et al. |
| 9,833,526 B2 | 12/2017 | Agafonov et al. |
| 9,903,673 B1 | 2/2018 | Dirks et al. |
| 2003/0227394 A1 | 12/2003 | Rothgeb et al. |
| 2008/0245788 A1 | 10/2008 | Choong et al. |
| 2011/0057123 A1 | 3/2011 | Ho |
| 2011/0203131 A1 | 8/2011 | Armstrong |

(Continued)

FOREIGN PATENT DOCUMENTS

| CN | 201722525 U | 1/2011 |
|---|---|---|
| CN | 102021782 A | 4/2011 |

(Continued)

*Primary Examiner* — Marc Lorenzi
(74) *Attorney, Agent, or Firm* — Price Heneveld LLP

(57) ABSTRACT

A sanitation system includes a drum configured to be positioned within a body of an appliance. The drum includes a lifter on an interior surface. A sanitation device is selectively disposed within the drum. The sanitation device includes a housing. A heatsink is integrally formed with the housing. The heatsink and the housing form an outer structure free of apertures. A sensor assembly is disposed within the outer structure. The sensor assembly includes a humidity sensor configured to sense humidity. A light source is disposed within the outer structure.

9 Claims, 9 Drawing Sheets

(56) References Cited

U.S. PATENT DOCUMENTS

| | | |
|---|---|---|
| 2012/0047763 A1 | 3/2012 | Abramovich et al. |
| 2012/0085133 A1 | 4/2012 | Slutsky et al. |
| 2015/0209457 A1 | 7/2015 | Bonutti et al. |
| 2015/0211165 A1 | 7/2015 | Willey et al. |
| 2015/0299933 A1 | 10/2015 | Oh |
| 2016/0074547 A1 | 3/2016 | Dobrinsky et al. |
| 2016/0146536 A1 | 5/2016 | Hoffman et al. |
| 2017/0226679 A1 | 8/2017 | De Bernardo et al. |
| 2019/0264372 A1 | 8/2019 | Kessler et al. |
| 2020/0069146 A1 * | 3/2020 | Kessler ............... A47L 15/4445 |

FOREIGN PATENT DOCUMENTS

| | | | |
|---|---|---|---|
| CN | 106012406 | A | 10/2016 |
| CN | 205917482 | U | 2/2017 |
| CN | 107044032 | A | 8/2017 |
| EP | 1960585 | A1 | 8/2008 |
| KR | 20060036664 | A | 5/2006 |
| KR | 20080088273 | A | 10/2008 |
| KR | 101747408 | B1 | 6/2017 |
| KR | 101862515 | B1 | 5/2018 |
| KR | 20180066460 | A | 6/2018 |
| TW | M378242 | U | 4/2010 |
| WO | 2010051808 | A3 | 5/2010 |
| WO | 2018011168 | A1 | 1/2018 |
| WO | 2018114358 | A1 | 6/2018 |

\* cited by examiner

SANITATION DEVICE

CROSS-REFERENCE TO RELATED APPLICATION

This application is a divisional of and claims priority to U.S. patent application Ser. No. 16/144,453, filed Sep. 27, 2018, now U.S. Pat. No. 11,085,147, and entitled "SANITATION DEVICE," the entire disclosure of which is incorporated herein in its entirety.

FIELD OF THE DISCLOSURE

The present disclosure generally relates to sanitation devices, and more particularly, to sanitation devices for sanitizing fabrics employing ultraviolet radiation.

BACKGROUND OF THE DISCLOSURE

Cleaning fabrics can be problematic when bacteria and/or other pathogens attached to one fabric may spread to other fabrics and thereby infect an entire load of laundry. Common bacteria and/or pathogens that may be present in laundry can typically include *Staphylococcus, Staphylococcus aureus, Pseudomonas aeruginosa, Escherichia coli,* and *Klebsiella pneumoniae.*

Given that laundry appliances frequently use rotating inner cavities, water, and air, the current solutions for sanitizing laundry do not sufficiently coincide with the latest consumer awareness in hygiene, health, and environmental safety. The most common attempts have been made to sanitize fabrics with chemical agents. However, such chemical agents often result in fabric discoloration, color fading, wrinkling, and/or bad odors. Many of the treatment chemicals also require extra precautions to be taken by the consumer to ensure safety, disposal of the treatment chemicals, and sufficient laundry cleaning. Further, the compatibility of the chemicals with different types of fabric has been difficult.

Accordingly, new solutions that offer improved techniques to sanitize fabrics and other objects within a washing or during a drying cycle of an appliance are needed. It is therefore desired to implement new approaches, devices, and/or cleaning agents to be used in appliances for safe, efficient, and affordable sanitation applications.

SUMMARY OF THE DISCLOSURE

According to one aspect of the present disclosure, a sanitation system includes a drum configured to be positioned within a body of an appliance. The drum includes a lifter on an interior surface. A sanitation device is selectively disposed within the drum. The sanitation device includes a housing. A heatsink is integrally formed with the housing. The heatsink and the housing form an outer structure free of apertures. A sensor assembly is disposed within the outer structure. The sensor assembly includes a humidity sensor configured to sense humidity. A light source is disposed within the outer structure.

According to another aspect of the present disclosure, a sanitation system includes a first housing. A heatsink is integrally formed with the first housing. The heatsink and the first housing form an outer structure free of apertures. A second housing is coupled to an outer surface of the outer structure. A sensor assembly is disposed within an interior of the outer structure. A light source is disposed within the interior of the outer structure. A controller is in communication with the sensor assembly and the light source.

According to yet another aspect of the present disclosure, an appliance includes a body. A drum is disposed within the body. The drum has an interior surface. A sensor assembly is coupled to the interior surface of the drum. The sensor assembly is configured to detect humidity and temperature within the drum. A light source is coupled to the sensor. The light source emits ultraviolet light. A controller is operatively coupled to the sensor assembly and configured to communicate with the sensor assembly.

These and other aspects, objects, and features of the present disclosure will be understood and appreciated by those skilled in the art upon studying the following specification, claims, and appended drawings.

DETAILED DESCRIPTION OF THE PREFERRED EMBODIMENTS

Figure 1:
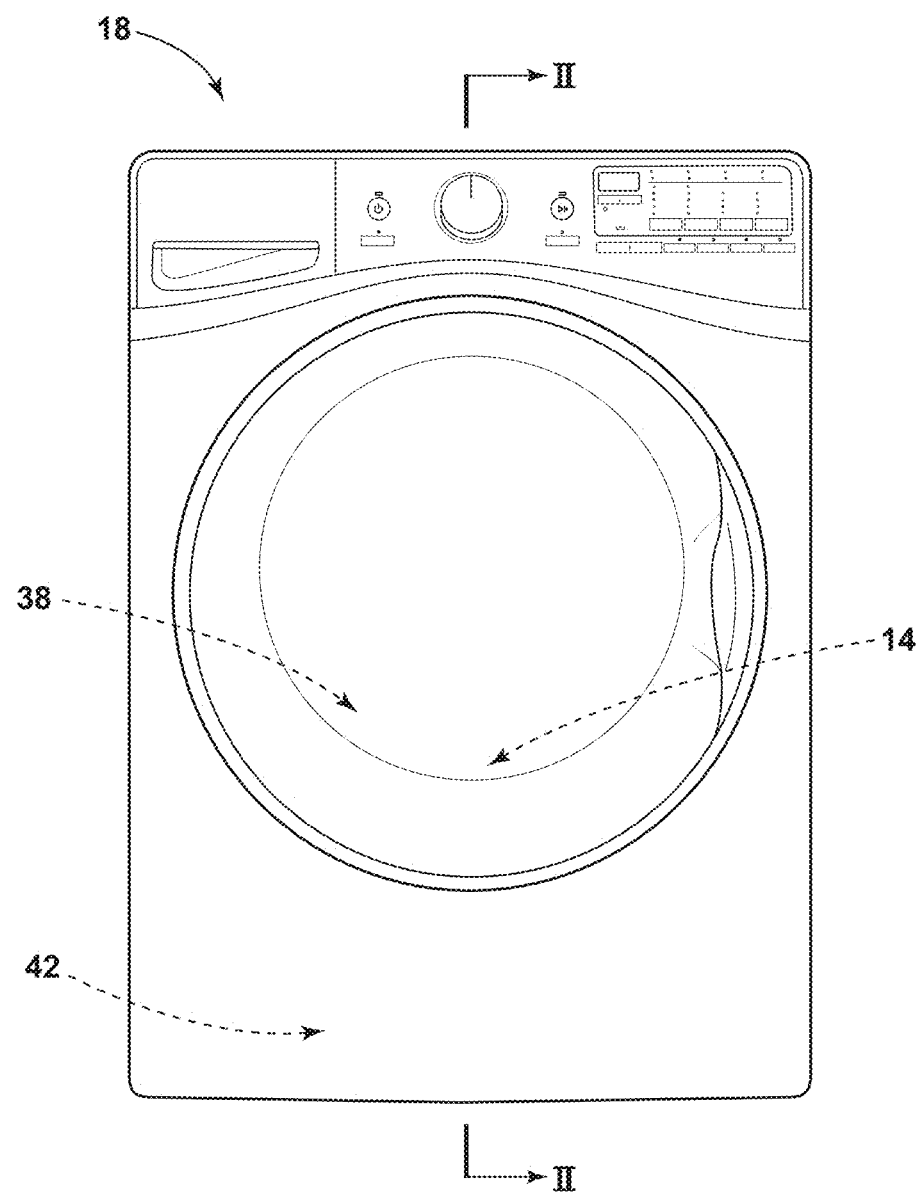
FIG. 1 is a front view of a laundry drying appliance according to some embodiments of the present disclosure.

For purposes of description herein, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

As required, detailed embodiments of the present disclosure are disclosed herein. However, it is to be understood that the disclosed embodiments are merely exemplary of the disclosure that may be embodied in various and alternative forms. The figures are not necessarily to a detailed design and some schematics may be exaggerated or minimized to show function overview. Therefore, specific structural and functional details disclosed herein are not to be interpreted as limiting, but merely as a representative basis for teaching one skilled in the art to variously employ the present disclosure.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Ranges can be expressed herein as from "about" one particular value, and/or to "about" another particular value. As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error, and the like, and other factors known to those skilled in the art. When the term "about" is used in describing a value or an end-point of a range, the disclosure should be understood to include the specific value or end-point referred to. Whether or not a numerical value or end-point of a range in the specification recites "about," the numerical value or end-point of a range is intended to include two embodiments: one modified by "about" and one not modified by "about." It will be further understood that the endpoints of each of the ranges are significant both in relation to the other endpoint, and independently of the other endpoint.

Referring to FIGS. 1-9, reference numeral 10 generally refers to a sanitation device that may be used to sanitize laundry 14 within an appliance 18. The sanitation device 10 can include a sensor assembly 22. The sensor assembly 22 may be positioned within a first housing 26 and can be configured to detect humidity, temperature, and/or color pigmentation. The sanitation device 10 may include a light source 30 where the light source 30 may emit ultraviolet (UV) light 30a. The sanitation device 10 may include a controller 34. The controller 34 may be coupled to the sensor assembly 22 and configured to send and/or receive information from the sensor assembly 22. In some embodiments, the appliance 18 may be a laundry appliance.

Figure 2:
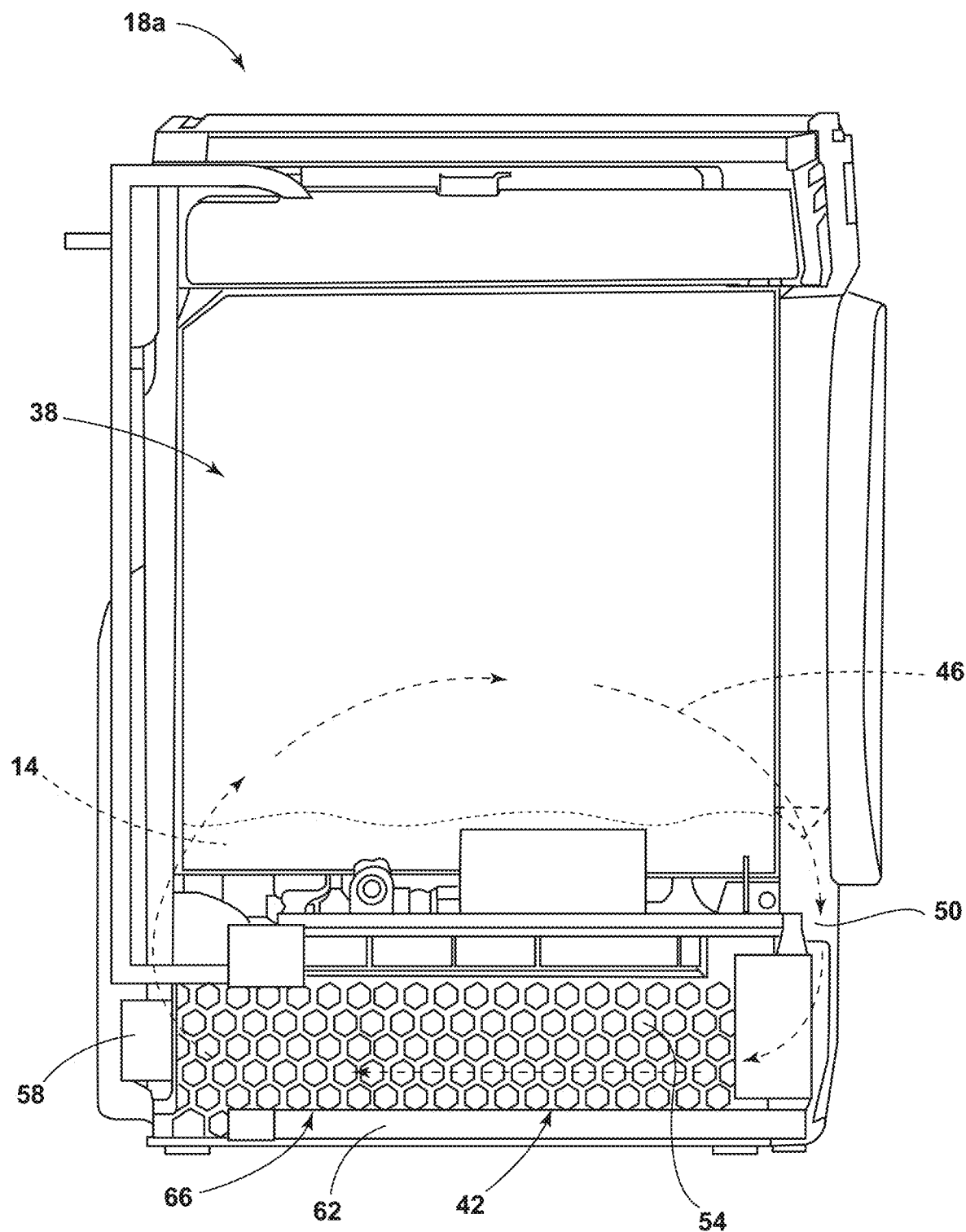
FIG. 2 is a cross-sectional view of the laundry drying appliance of FIG. 1 taken along the line II-II.

As exemplified in FIGS. 1 and 2, the appliance 18 for processing laundry 14 within a drum 38 of the appliance 18 is shown. In some embodiments, the appliance 18 may be a laundry drying appliance 18a. To assist in processing the laundry 14 within the drum 38, a heat pump system 42 can be configured to condition process air 46 that is moved through an airflow path 50. The heat pump system 42 may include one or more heat exchangers 54, which may be in the form of an evaporator and a condenser. The heat exchangers 54, in the form of evaporators, may be configured to dehumidify process air 46 that is delivered from the drum 38. The process air 46 delivered from the drum 38 can include moisture and lint particles that are carried away from the load of laundry 14 and are moved by a blower 58 through the airflow path 50 to the heat exchangers 54. The heat exchangers 54, in the form of condensers, of the heat pump system 42 can reject heat from a surface of the condenser and deliver this heat into the process air 46. The process air 46 may thereby be heated and then delivered back to the drum 38 for continuing the processing of laundry 14. The blower 58 of the laundry drying appliance 18a can deliver process air 46 through the airflow path 50 that includes the rotating drum 38 and the various heat exchangers 54 of the heat pump system 42.

Referring still to FIGS. 1 and 2, during performance of a particular drying cycle, moisture can be removed from the load of laundry 14 and moved to the heat exchangers 54 where the removed moisture can form condensation that may be captured within a drain channel 62 of the laundry drying appliance 18a. Additionally, various other residual fluids 66, including moisture, water vapor, and condensation in the drain channel 62, can be captured or otherwise deposited within portions of the airflow path 50 and can remain within the airflow path 50 after completion of the drying cycle. It should be appreciated that in alternative embodiments, a washing machine or a combination washing machine/dryer may be used without departing from the teachings herein.

Figure 3:
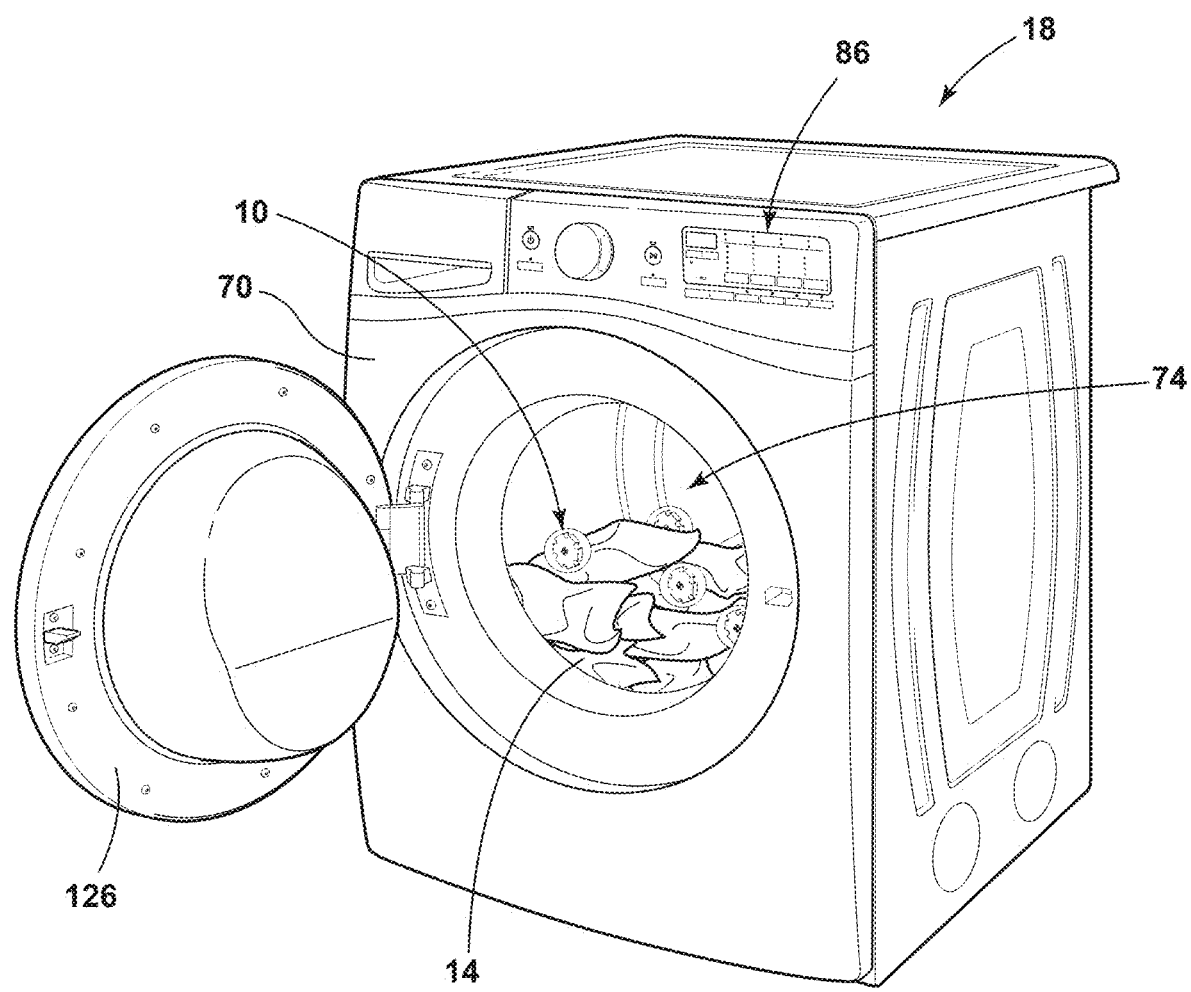
FIG. 3 is a front view of an appliance having a plurality of sanitation devices included according to some embodiments of the present disclosure.

Referring to FIG. 3, the appliance 18 is shown with the load of laundry 14 therein. In some embodiments, the appliance 18 has a body 70 defining a cavity 74. In other embodiments, the appliance 18 has the body 70 enclosing the drum 38 having a lifter 78 (FIG. 7) and/or a drum paddle coupled to an interior surface 82 of the drum 38. The lifter 78 may be integrated within the drum 38 or may be fixedly or removably attachable to the interior surface 82 of the drum 38. The appliance 18 can have a control panel 86 configured to operate the appliance 18. It should be appreciated that the appliance 18 may be a washing machine, dryer, or other appliance that may utilize sanitation processes without departing from the teachings herein.

Referring still to FIG. 3, in some embodiments, it may be advantageous to use a plurality of sanitation devices 10 in a single load of laundry 14 to increase sanitation of regular and/or larger loads of laundry 14. The sanitation device 10 may be charged to have sufficient power to operate during a portion of or all of the appliance cleaning cycle (e.g. a wash or dry cycle). Once charged, the sanitation device 10 can be positioned inside the appliance 18 with the laundry 14. The appliance door 126 can be closed and a selected cycle started. The activation of the appliance 18 may act in combination with the controller 34 and/or the sensor assembly 22 to activate the sanitation device 10 through motion and/or information received by the sensor assembly 22. In some embodiments, the light source 30 is capable of emitting UV-A (~320-400 nanometers) and UV-C (~100-290 nanometers) light to disrupt the outer membranes of microbes.

Still referring to FIG. 3, in some embodiments, the sanitation device 10 may be used in a washing machine. In other embodiments, the sanitation device 10 can be used in a dryer. In yet other embodiments, the sanitation device 10 may be used in both washing machines and dryers.

Figure 4:
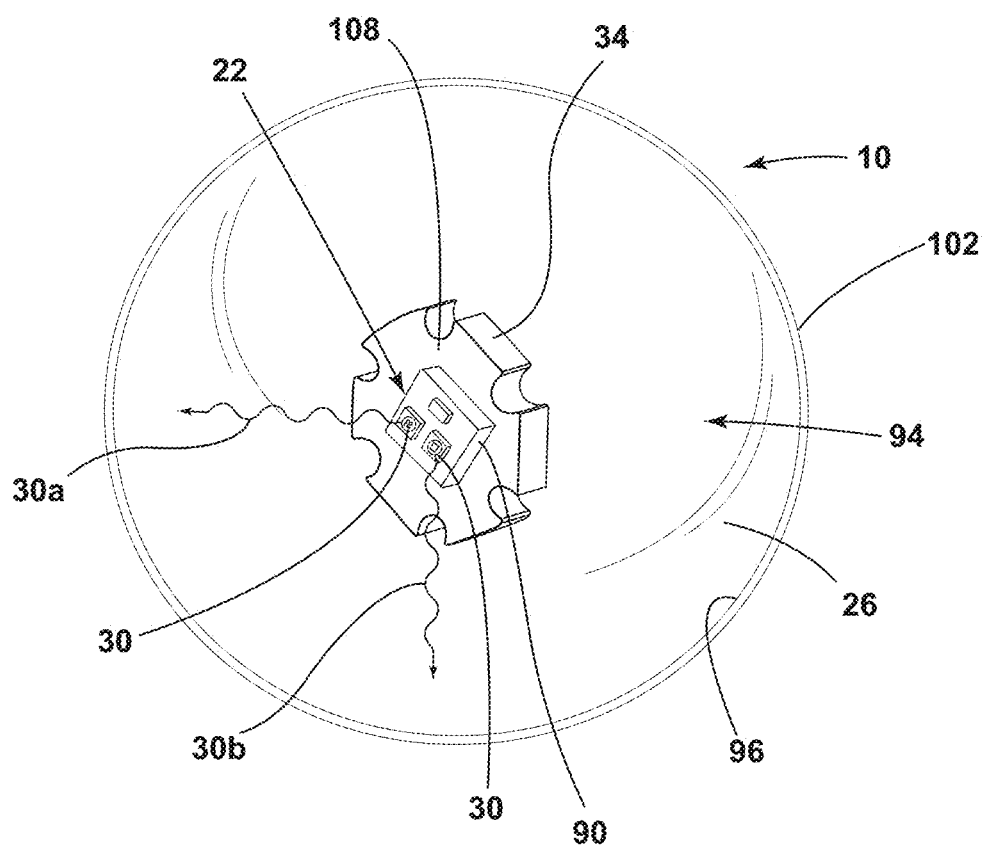
FIG. 4 is a front view of a sanitation device, according to some embodiments of the present disclosure.

Referring to FIGS. 3 and 4, included with the load of laundry 14 may be the sanitation device 10, which may tumble with the load of laundry 14 providing close proximity of the sanitation device 10 to the laundry 14 to help facilitate sanitation of the fabrics. In some embodiments, sanitation device 10 may include the light source 30, which may be configured to emit a combination of UV-A (~320-400 nanometers), UV-B (~280-320 nanometers), and/or UV-C (~100-290 nanometers) light to sanitize the load of laundry 14. In other embodiments, the light source 30 may emit UV-A and/or UV-C light. In still other embodiments, the light source 30 may emit UV-C light. When the appliance 18 is in use, there may be substrates in the air within the drum 38 and/or combined with water, which may include, but is not limited to, water compounds, soil, chemicals, and detergent. In some embodiments, the UV-A light acts as an airborne disinfectant and the UV-C light acts as a disinfectant of fabrics, where the UV radiation can create a cascade of biological events, including of microbial deoxyribonucleic acid (DNA) damaging and rupturing outer membranes of the microbes. In various embodiments, the light source 30 may be, for example, a III-nitride wide bandgap semiconductor UV light emitting diode (LED) source capable of emitting UV light 30*a* having a wavelength between about 330 nanometers to about 380 nanometers, where the selected range of UV light 30*a* may increase sanitation of laundry 14 through disinfecting fabrics from pathogens and/or bacteria. In some embodiments, sanitation is accomplished through LED light rays from the light source 30. In other embodiments, the light source 30 may emit UV-C light within a washing machine. In yet other embodiments, the light source 30 may emit UV-A and UV-C light within a dryer.

Referring still to FIGS. 3 and 4, the sanitation device 10 is shown according to some embodiments. The sanitation device 10 can include the sensor assembly 22 positioned within the first housing 26. The first housing 26 may be any shape including, for example, spherical, cylindrical, oblique, torrid, etc. In some embodiments, the spherical shape may be advantageous such that the sanitation device 10 can better minimize getting caught within the load of laundry 14 during a washing or drying cycle so the sanitation device 10 is better circulated throughout the laundry 14. The first housing 26 may be made from a wide range of materials, including, but not limited to, plastic, acrylic, plexiglass, polypropylene, polycarbonate, or any other similar material. In some embodiments, the first housing 26 may be made of a transparent medium, about 0% transparent, about 25-100% transparent, about 40-100% transparent, about 50-100% transparent, about 60-95% transparent, about 70-90% transparent, about 80-95% transparent, or about 80-90% transparent so the UV and/or visible light 30*a*, 30*b* may be emitted through the first housing 26 into the appliance 18.

Figure 6:
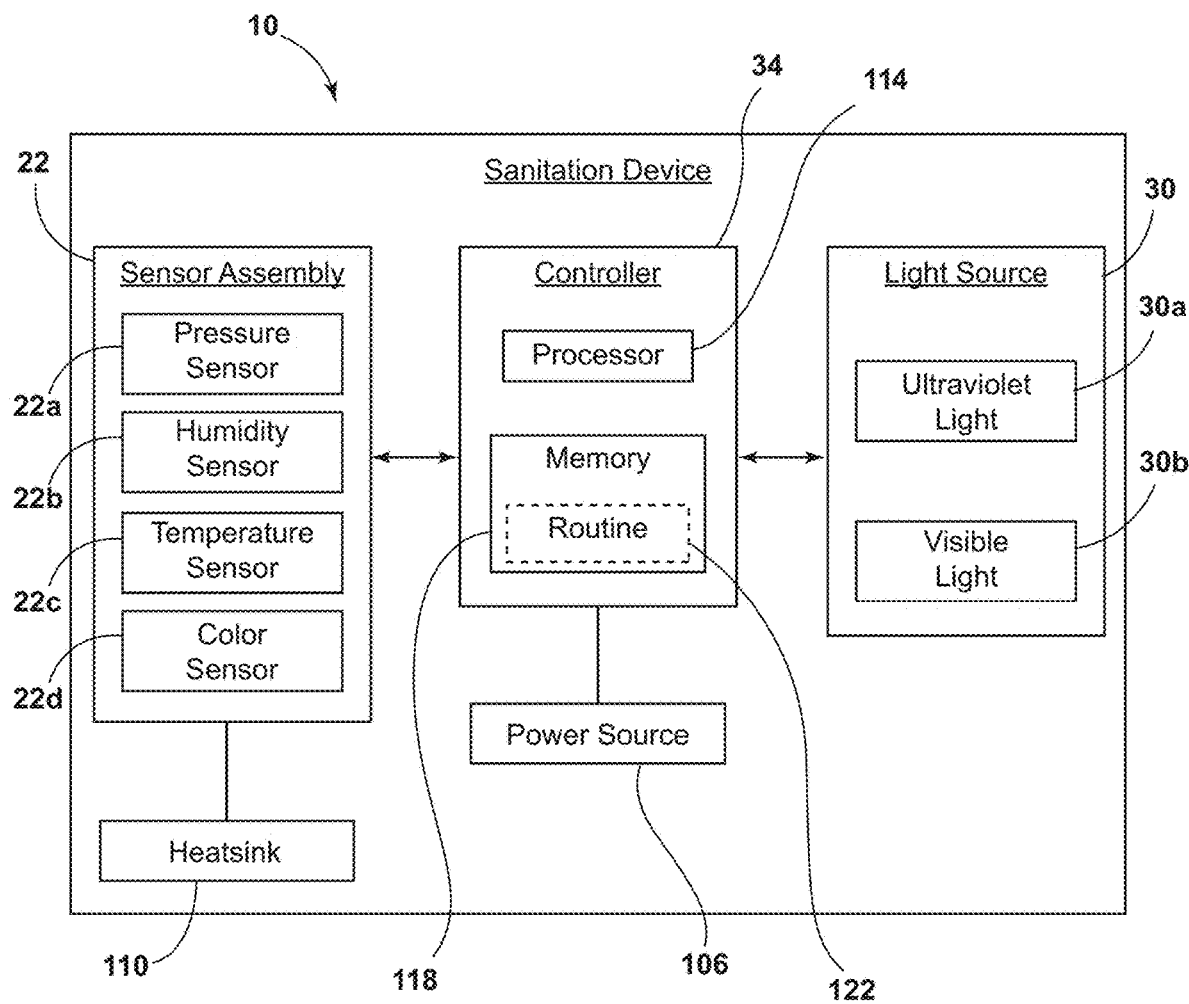
FIG. 6 is a schematic flow diagram of a controller used in the sanitation device according to some embodiments of the present disclosure.

Referring to FIG. 4, the sensor assembly 22 may be coupled to a printed circuit board (PCB) 90. In various embodiments, the sensor assembly 22, the PCB 90, and/or a combination thereof may be positioned within the first housing 26. In some embodiments, the sensor assembly 22 may be embedded within an interior 94 of the first housing 26. The sensor assembly 22 may be configured to detect, for example, humidity, temperature, color pigmentation, and/or any combination thereof. It should be appreciated that the sensor assembly 22 may have one sensor or a number of sensors configured to detect humidity, temperature, and/or color pigmentation without departing from the teachings herein. In various embodiments, the sensor assembly 22 may be configured to detect humidity and/or temperature within the cavity 74 of the appliance 18. Sensing temperature and/or humidity within the appliance 18 may be advantageous to allow a user to know when the appliance cycle (e.g. a wash or dry cycle) is completed or if the laundry 14 has not sufficiently dried. Such capabilities may also be advantageous to signal that the sanitation device 10 should continue sanitation of the laundry 14 until a certain temperature and/or humidity is achieved. Detection of the color pigmentation of fabrics may be advantageous to help sanitize the fabrics without compromising the relative color of the fabrics. In some embodiments, the sensor assembly 22 may include infrared sensors such that the sensor assembly 22 may detect information from its surroundings through the transparent first housing 26. In other embodiments, the sensor assembly 22 may include a pressure sensor 22*a*, humidity sensor 22*b*, temperature sensor 22*c*, and/or color sensor 22*d* (FIG. 6). In yet other embodiments, the sensor assembly 22 may include a sensor and/or sensors with a single wire digital interface integrated on a microchip. The sensor assembly 22 may be operatively or electrically coupled to the controller 34 and can be configured to send and/or receive information from the controller 34. In some embodiments, the sensor assembly 22 is configured to detect color pigmentation of fabrics using the color sensor 22*d*. In other embodiments, the sensor assembly 22 is configured to detect temperature, humidity, and/or a combination thereof using the humidity sensor 22*b* and temperature sensor 22*c*, respectively, within the drum and is configured to send information to the controller 34.

Referring still to FIG. 4, the PCB 90 may be positioned on the controller 34, or otherwise positioned within the first housing 26, and includes a control having control circuitry with light source drive circuitry for controlling activation and deactivation of the light source 30. In various embodiments, the PCB 90 may be coupled to a first surface 108 of the controller 34. In other embodiments, the sensor assembly 22 and the light source 30 may be coupled to the PCB 90 which is coupled to the first surface 108 of the controller 34. The PCB 90 may be any type of circuit board including, but not limited to, a flexible PCB and/or rigid PCB. In alternate embodiments, the control may be positioned externally from the first housing 26 without departing from the scope of the present disclosure. In various embodiments, the PCB 90 may be enclosed within a support structure.

Figure 5:
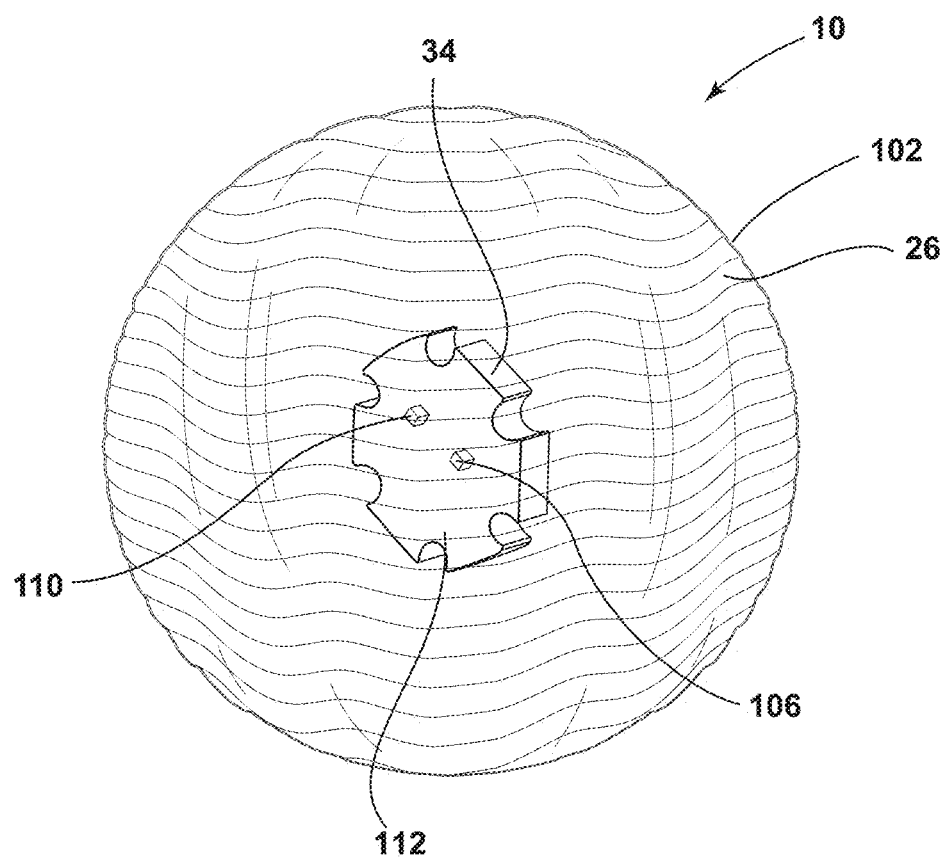
FIG. 5 is a rear view of a sanitation device, according to some embodiments of the present disclosure.
Figure 9:
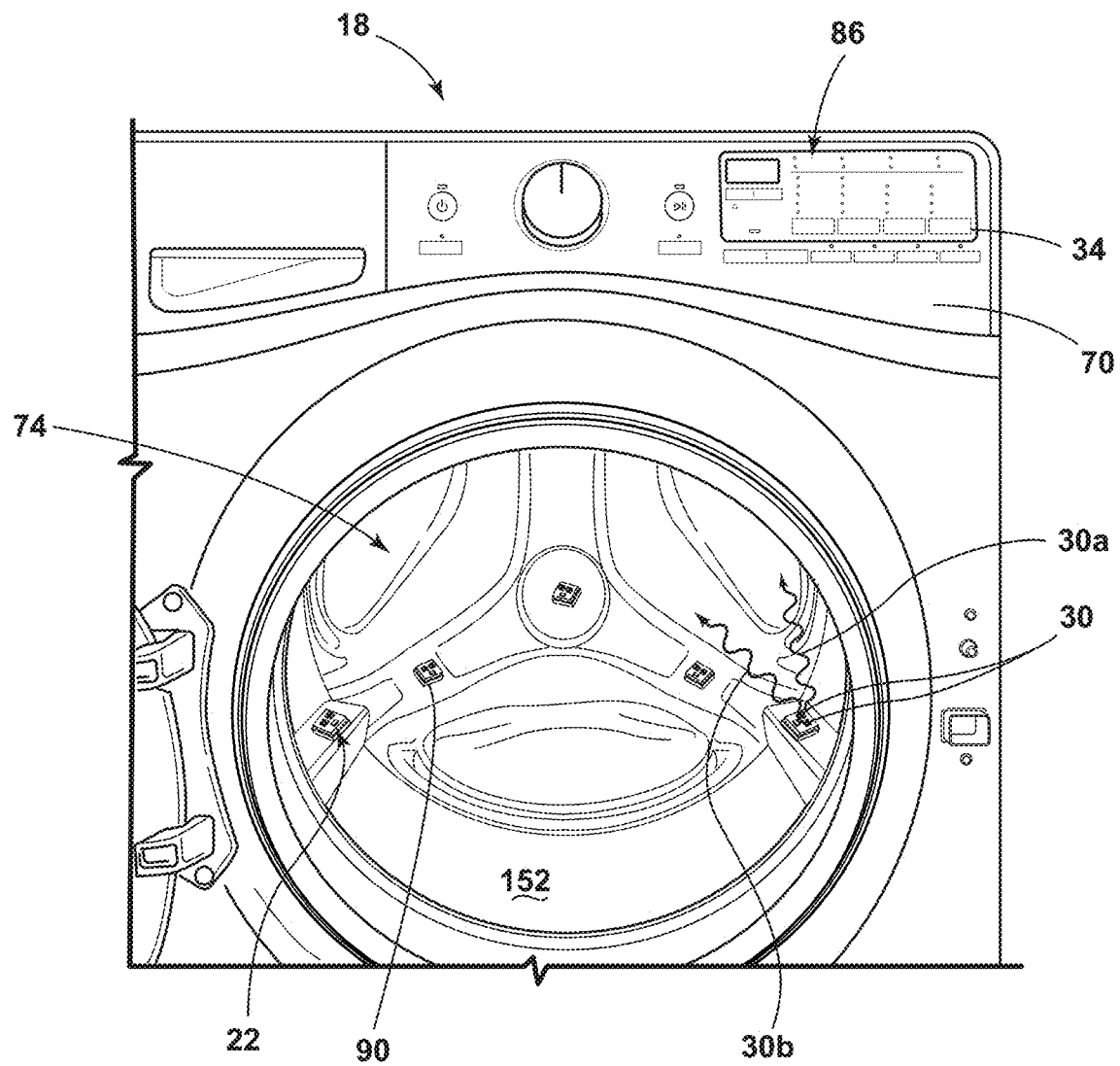
FIG. 9 is a partial view of the appliance having a sensor assembly and a light source coupled to an interior surface of the appliance according to some embodiments.

In some embodiments, the controller 34 may be positioned within the first housing 26 of the sanitation device 10 and may be coupled to the power source 106 (FIG. 5). The controller 34 may be a microchip and/or a cross-sectional disk embedded into the first housing 26. In other embodiments, the controller may be molded into the first housing 26. In yet other embodiments, the first housing 26 may be partially and/or substantially hollow and the controller 34 may be coupled to an interior surface 96 of the first housing 26. In alternate embodiments, the controller 34 may be positioned on the body 70 of the appliance 18 (FIG. 9).

Still referring to FIG. 4, the sanitation device 10 includes the light source 30. The light source 30 may be positioned within the first housing 26 and coupled to the PCB 90. In various embodiments, the light source 30 may be operatively or electrically coupled to the controller 34 and may be configured to send and/or receive information from the controller 34. In some embodiments, the light source 30 is configured to emit UV light 30*a* or a comparable light thereof. The UV light 30*a* may have a wavelength between about 300 nanometers to about 380 nanometers to help prevent fading of fabric color pigmentation.

With further reference to FIG. 4, in other embodiments, the light source 30 may be configured to emit visible light 30*b* or a comparable light thereof. The light source 30 may include, but is not limited to, fluorescent lighting, light emitting diodes (LEDs), organic LEDs (OLEDs), polymer LEDs (PLEDs), solid-state lighting, or any other form of lighting configured to emit visible light 30*b*. The use of UV LEDs takes advantage of the relatively low cost of LEDs. In some embodiments, the light emitting device known in the art configured to emit visible light 30*b* may be 4750K correlated color temperature (CCT) white LEDs. In some embodiments, the light source is configured to emit visible light 30*b* and ultraviolet light 30*a*, where the ultraviolet light 30*a* has a wavelength between about 300 nm to about 380 nm to help prevent color alteration of fabrics. In other embodiments, wherein the light source 30 is configured to emit both UV-A and UV-C light.

The light source 30 may be operatively or electrically coupled to the pressure sensor 22a within the sensor assembly 22 (FIG. 6). In some embodiments, the pressure sensor 22a can be effected when the sanitation device 10 moves about the drum 38 of the appliance 18. The pressure sensor 22a may then act in combination with the sensor assembly 22 and/or the controller 34 to activate the light source 30 during the appliance cycle (e.g. a wash or dry cycle). This can allow for sanitation of the laundry 14 and/or appliance 18 when the light source 30 emits UV light 30a. This can also help a user see within the appliance 18 during a cycle when the light source 30 emits visible light 30b. In some embodiments, the light source 30 emits visible light 30b when the appliance 18 is in use.

Referring to FIG. 5, the sanitation device 10 may have a power source 106. The power source 106 may be coupled to the sensor assembly 22 and/or the controller 34 (FIG. 6). The power source 106 may be positioned within the first housing 26 or integrated into the first housing 26. In other embodiments, the power source 106 may be integrated into the second housing 130. In some embodiments, the power source 106 may be coupled to a second surface 112 of the controller 34. In various embodiments, the sensor assembly 22 and the light source 30 (FIG. 4) may be coupled to the first surface 108 of the controller 34 and the power source 106 may be coupled to the second surface 112 of the controller 34, wherein the first surface 108 and the second surface 112 are opposing surfaces. The power source 106 may include any direct current (DC) generating device, including, but not limited to, a lithium-ion battery. In some embodiments, the power source 106 may be rechargeable. The power source 106 may be capable of withstanding temperatures up to about 65° C., 85° C., 100° C., 125° C., or 150° C. In various embodiments, the power source 106 may be a rechargeable high temperature battery coupled to the light source 30 and the PCB 90. In some embodiments, the rechargeable battery may be compact and light in weight (e.g., about 5-10 grams, about 10-20 grams, about 20-50 grams, about 50-100 grams, about 100-200 grams, or about 200-300 grams). The power source 106 will be capable of withstanding temperatures greater than the desired application or specific laundry appliances without departing from the teachings herein. In some embodiments, the power source 106 can be a rechargeable battery capable of withstanding temperatures up to about 150° C.

With further reference to FIG. 5, in some embodiments, the power source 106 may be configured to charge using the motion and/or induction provided by the respective appliance 18. In other embodiments, the power source 106 may be charged by a charging member, such that placing the sanitation device 10 on the charging member will allow the sanitation device 10 to charge. In various embodiments, the charging member may be a remote cordless charging member that charges the power source 106. In some embodiments, the sanitation device 10 may be powered to last a full cycle of the appliance 18, which may be between about 45 minutes to about 1.5 hours. In other embodiments, a full charge on the sanitation device 10 may last for several wash and/or dry cycles. In some embodiments, the power source 106 is coupled to the sensor assembly 22, wherein the power source 106 is configured to charge using motion, induction, and/or a combination thereof. In other embodiments, the power source 106 is coupled to the first housing 26 and capable of withstanding temperatures up to about 150° C.

Still referring to FIG. 5, the sanitation device may include a heatsink 110. The heatsink 110 may be positioned on an outer surface 102 of the first housing 26. In other embodiments the heatsink 110 may be integrally formed with the first housing 26 such that the heatsink 110 and first housing 26 form one continuous piece. In yet other embodiments, the heatsink 110 may be positioned the interior 94 of the first housing 26. In some embodiments, the heatsink 110 may be exposed between the second housing 130. In yet other embodiments, the heatsink 110 may be coupled to the second surface 112 of the controller 34. In various embodiments, the heatsink 110 may be coupled to the sensor assembly 22 (FIG. 6) and/or positioned proximate the sensor assembly 22. In some embodiments, the heatsink 110 may be configured to dissipate and/or transfer thermal energy proximate the sensor assembly 22 such that the sensor assembly 22 may detect temperature. In other embodiments, condensation may form on the heatsink 110 and the heatsink 110 may be positioned proximate the sensor assembly 22 such that the sensor assembly 22 may detect humidity. The heatsink 110 may be made from, for example, reflective aluminum, aluminum alloy, or other reflective and/or conductive metal materials. In some embodiments, the heatsink 110 is coupled to the first housing 26 and coupled to the sensor assembly 22, wherein the heatsink 110 is configured to transfer thermal energy proximate the sensor assembly. In various embodiments, the sanitation device 10 does not include the heatsink 110.

Still referring to FIG. 5, in some embodiments, the first housing 26 may have alternating diameters. In various embodiments, the first housing 26 may be corrugated having ridges and grooves. In other embodiments, the first housing 26 may have a constant diameter (FIG. 4).

Referring to FIG. 6, the controller 34 can be configured to send and/or receive information from the sensor assembly 22. In various embodiments, the controller 34 may be electrically or operatively connected to the sensor assembly 22. The sensor assembly 22 may include one or more sensors, including, but not limited to, the pressure sensor 22a, the humidity sensor 22b, the temperature sensor 22c, the color sensor 22d, and/or a combination thereof. The controller 34 may also be electrically or operatively coupled the light source 30, wherein the light source 30 may emit UV light 30a and/or visible light 30b (FIG. 4). The controller 34 may be configured to send and/or receive information from the sensor assembly 22, the light source 30, and/or a combination thereof. In some embodiments, the controller 34 of the sanitation device 10 may be configured to send information to a user device to update the user on the status of the appliance, cleaning cycle, sanitation process, and/or combination thereof.

Referring still to FIG. 6, in some embodiments, the controller 34 includes a memory 118 and a processor 114. The memory 118 can contain a routine 122 for operation of the controller 34. The processor 114 is coupled to the memory 118 and is configured to execute the routines 122 contained in the memory 118.

In a specific example, the sanitation device 10 may include the sensor assembly 22, having the humidity sensor 22b, the temperature sensor 22c, and the color sensor 22d. The sanitation device 10 may also include a light source 30 configured to emit UV light 30a and visible light 30b, wherein the sensor assembly 22 and light source 30 may be embedded within the first housing 26 that is made of silicone. The sanitation device 10 may include the power source 106, wherein the power source 106 may be a high temperature rechargeable battery configured to be charged through the cordless charging member. Information detected from the humidity sensor 22b, the temperature sensor 22c, and/or the color sensor 22d may be displayed through a human-machine interface (HMI) fascia indicator and/or relayed to a consumer mobile device.

Figure 7:
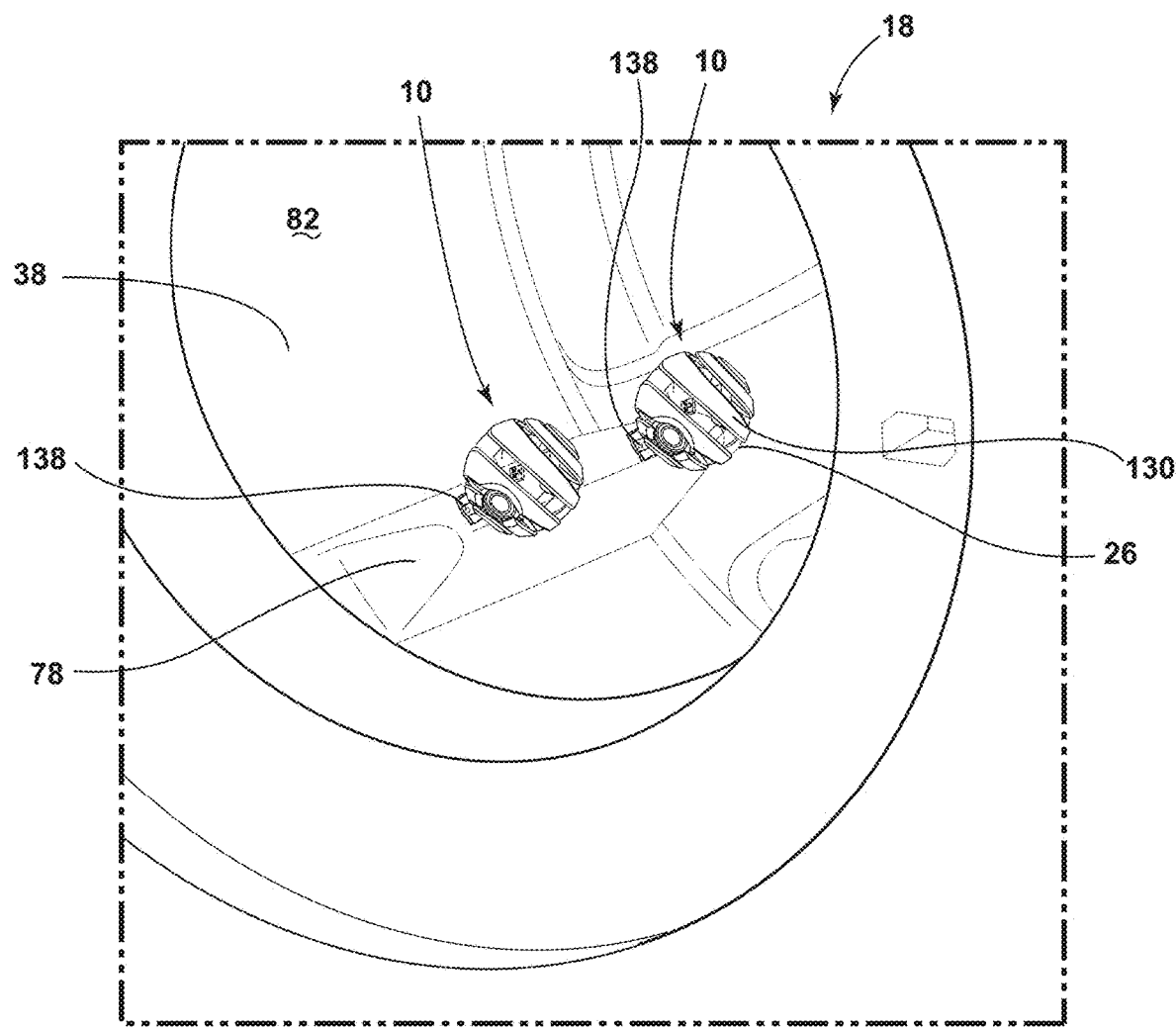
FIG. 7 is a partial view of the appliance having the sanitation device removably attachable to a lifter coupled to an interior surface of the appliance according to some embodiments.

Referring to FIG. 7, the sanitation device 10 may be removably attachable to the lifter 78 coupled to the interior surface 82 of the drum 38 of the appliance 18, which may be advantageous to help prevent the sanitation device 10 from being caught within the laundry 14 while it is being washed and/or dried (FIG. 3). An attachment feature 138 may be used to attach the sanitation device 10 to the lifter 78. The attachment feature 138 may be, but is not limited to, a pin, adhesive, fastener, snap, buckle, or other feature for temporary and/or repeated attachment sufficient to secure the sanitation device 10 to the lifter 78 when the appliance 18 is in use.

With further reference to FIG. 7, the sanitation device 10 may include a second housing 130 coupled to the outer surface 102 (FIG. 4) of the first housing 26. The second housing 130 may cover all or a portion of the first housing 26. In other embodiments, the second housing 130 may be made of silicone, UV transparent silicone, rubber, polyurethane, polyisoprene, nitrile, or other elastomeric known in the art materials. The second housing 130 may act as bumper providing physical protection for the sanitation device 10 as it tumbles about the drum 38 of the appliance 18 (FIG. 3). In some embodiments, the second housing 130 may be a variety of different colors. In other embodiments, the second housing 130 is coupled to an outer surface 102 (FIG. 5) of the first housing 26, wherein the second housing 130 covers a portion of the first housing 26 and the first and second housings 26, 130 are spherical. In some aspects, the second housing 130 can be a spiral band, concentric rings, and/or one or more bands where the first housing 26 is exposed to the cleaning environment.

Figure 8:
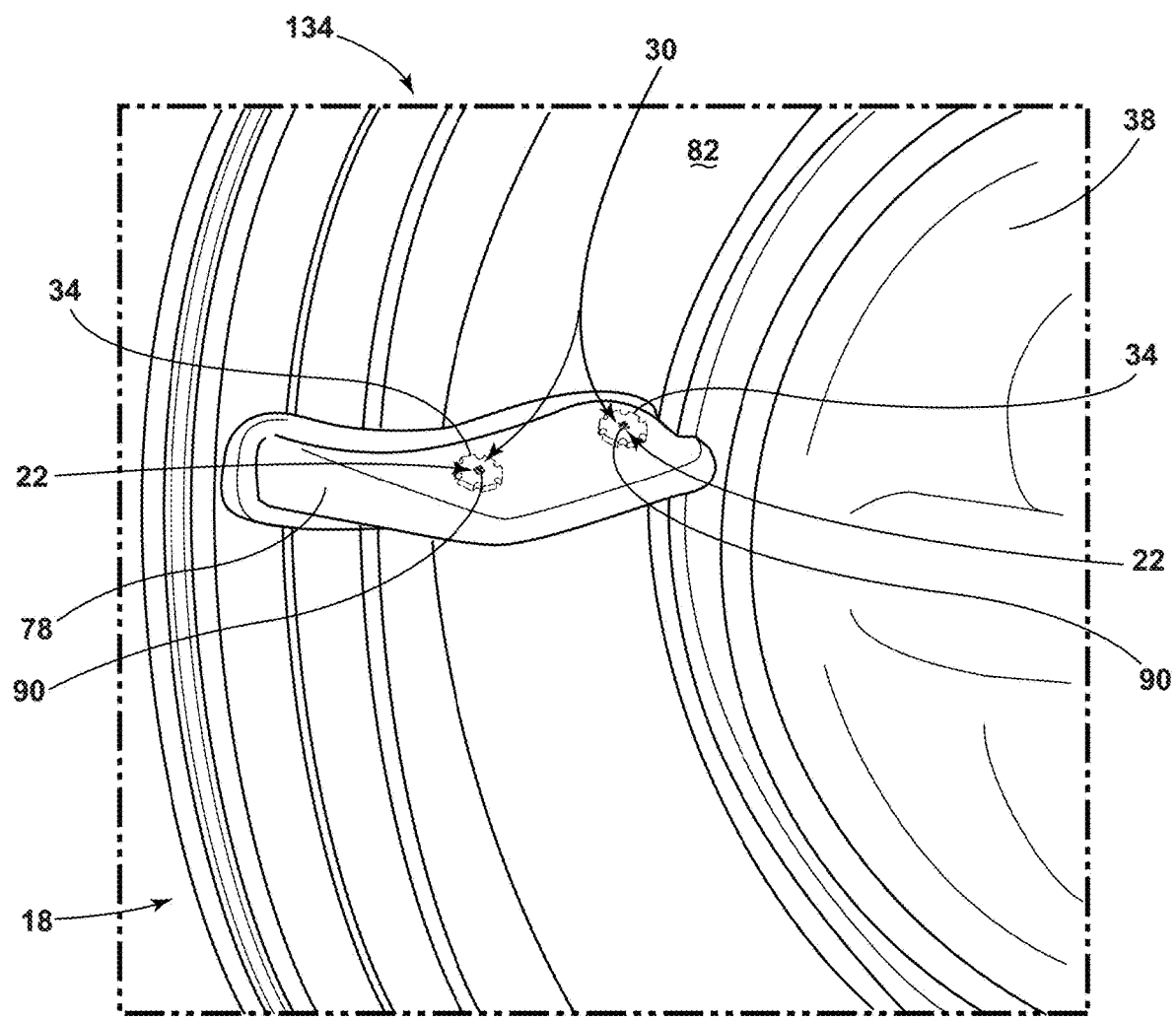
FIG. 8 is a partial view of an interior surface of the appliance having a sensor assembly attached to a lifter within an interior of the appliance according to some embodiments.

Referring to FIG. 8, a sanitation system 134 may include the appliance 18 enclosing the drum 38, where the drum 38 has the lifter 78 coupled to the interior surface 82 of the drum 38. The sensor assembly 22 may be removably coupled to the lifter 78. In other embodiments, the light source 30 may be coupled to the sensor assembly 22. In some embodiments the light source 30 may be positioned on the lifter 78 proximate the sensor assembly 22. In yet other embodiments, the light source 30 and/or the sensor assembly 22 may be coupled to the PCB 90. In some embodiments, the PCB 90 may be coupled to the lifter 78. In various embodiments, the PCB 90 may be coupled to the controller 34.

Referring still to FIG. 8, in some embodiments, the controller 34 may be positioned on the lifter 78 proximate the sensor assembly 22 and/or the light source 30. The controller 34 may be positioned within the first housing 26. In various embodiments, the controller 34 may be coupled to sensor assembly 22 and/or the light source 30 and configured to send and/or receive information from the sensor assembly 22 and/or the light source 30.

Referring to FIG. 9, the appliance 18 is shown having the body 70 defining the cavity 74. The sensor assembly 22 may be coupled to an interior surface 152 of the cavity 74. The sensor assembly 22 may be configured to detect humidity, temperature, and/or a combination thereof within the cavity 74. The sensor assembly 22 may be operatively or electrically coupled to the controller 34.

Still referring FIG. 9, the light source 30 can be coupled to the sensor assembly 22, wherein the light source 30 may be configured to emit UV light 30a, which may have a wavelength between about 300 nanometer to about 380 nanometer to help prevent color alteration of fabrics. In other embodiments, the light source 30 may emit visible light 30b or comparable light thereof, which may be configured to illuminate while the appliance 18 is in use. In yet other embodiments, the light source 30 may emit UV light 30a and visible light 30b. The light source 30 may include, but is not limited to, fluorescent lighting, light emitting diodes (LEDs), organic LEDs (OLEDs), polymer LEDs (PLEDs), solid-state lighting, or any other form of lighting configured to emit light. The light source 30 may be operatively or electrically coupled to the controller 34. The light source 30 can be coupled to the PCB 90, which contains a control having control circuitry with light source drive circuitry for controlling activation and deactivation of the light source 30. The PCB 90 may be any type of circuit board including, but not limited to, a flexible PCB and/or rigid PCB.

Referring still to FIG. 9, the controller 34 may be configured to send and/or receive information from the sensor assembly 22 and/or the light source 30. In some embodiments, the controller 34 may be positioned proximate to the sensor assembly 22 and/or the light source 30. In other embodiments, the controller 34 may be positioned in any location on the body 70 of the appliance 18, including, but not limited to, proximate to or positioned on the control panel 86.

With further reference to FIG. 9, in some embodiments, the sensor assembly 22 and/or the light source 30 may be fixedly mounted to the interior surface 152 of the cavity 74 of the appliance 18. The sensor assembly 22, the light source 30, and/or the controller 34 may be powered by the appliance 18, which may be advantageous to keep the sensor assembly 22 and/or the light source 30 in close proximity to the laundry 14 within the appliance 18 while preventing the sensor assembly 22 and/or light source 30 from getting caught within the laundry 14. In some embodiments, the sensor assembly 22 may be positioned within the first housing 26 and/or the second housing 130 (FIG. 8). In some embodiments, the first housing 26 is positioned about the sensor assembly 22 and coupled to the interior surface 152 of the cavity 74.

In a specific example, the PCB 90 may be a flatpack coupled to the light source 30 and the sensor assembly 22. The light source 30 may be configured to emit UV light 30a and visible light 30b. The sensor assembly may include the humidity sensor 22b, temperature sensor 22c, and color sensor 22d. The PCB 90, light source 30, and sensor assembly 22 may be coupled to the interior surface 152 of the cavity 74 of the appliance 18 and not embedded and/or positioned within the first housing 26. In another example, the PCB 90, light source 30, and sensor assembly 22 may be coupled to the lifter 78 (FIG. 8).

In yet other embodiments, the sensor assembly 22 may include a sensor and/or sensors with a single wire digital interface integrated on a microchip. The microchip may also include the light source 30 and be coupled to the PCB 90. The microchip may be directly mounted to the interior surface 152 of the cavity 74 of the appliance 18.

It will be understood by one having ordinary skill in the art that construction of the described disclosure, and other components, is not limited to any specific material. Other exemplary embodiments of the disclosure disclosed herein may be formed from a wide variety of materials, unless described otherwise herein.

For purposes of this disclosure, the term "coupled" (in all of its forms: couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature, or may be removable or releasable in nature, unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, and the nature or numeral of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes, or steps within described processes, may be combined with other disclosed processes or steps to form structures within the scope of the present disclosure. The exemplary structures and processes disclosed herein are for illustrative purposes and are not to be construed as limiting.

It is to be understood that variations and modifications can be made on the aforementioned structure without departing from the concepts of the present disclosure, and further it is to be understood that such concepts are intended to be covered by the following claims unless these claims by their language expressly state otherwise.

What is claimed is:

1. A sanitation system, comprising:
an appliance having a body and a drum positioned within the body of the appliance, wherein the drum includes a lifter on an interior surface thereof; and
a sanitation device selectively disposed within the drum, wherein the sanitation device includes:
a housing;
a heatsink integrally formed with the housing, wherein the heatsink and the housing form an outer structure free of apertures;
a sensor assembly disposed within the outer structure, wherein the sensor assembly includes a humidity sensor configured to sense humidity; and
a light source disposed within the outer structure, wherein the light source is configured to emit ultraviolet light for sanitizing.

2. The sanitation system of claim 1, wherein the sanitation device includes an attachment feature configured to selectively couple the sanitation device to the lifter.

3. The sanitation system of claim 1, wherein the light source is configured to emit visible light.

4. The sanitation system of claim 1, wherein the sensor assembly includes a temperature sensor configured to sense temperature within the drum.

5. The sanitation system of claim 1, wherein the sensor assembly includes a color sensor configured to sense color pigmentation of items disposed within the drum.

6. The sanitation system of claim 1, wherein the sensor assembly includes a pressure sensor configured to sense movement of the sanitation device within the drum.

7. The sanitation system of claim 6, further comprising:
a controller in communication with the sensor assembly and the light source, wherein the controller is configured to activate the light source in response to a signal from the pressure sensor.

8. The sanitation system of claim 1, wherein the housing is at least 50% transparent.

9. The sanitation system of claim 1, wherein the housing defines at least one of ridges and grooves.

* * * * *